United States Patent
Asfour et al.

(10) Patent No.: US 11,559,495 B1
(45) Date of Patent: Jan. 24, 2023

(54) ICARIIN NANO-PHARMACEUTICAL FORMULATION

(71) Applicant: King Abdulaziz University, Jeddah (SA)

(72) Inventors: Hani Z. Asfour, Jeddah (SA); Nabil A. Alhakamy, Jeddah (SA); Raed I. Felimban, Jeddah (SA); Osama A. A. Ahmed, Jeddah (SA); Waleed Y. Rizg, Jeddah (SA); Usama A. Fahmy, Jeddah (SA); Ashraf B. Abdel-Naim, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/687,754

(22) Filed: Mar. 7, 2022

(51) Int. Cl.
| | |
|---|---|
| A61K 9/51 | (2006.01) |
| A61K 47/10 | (2017.01) |
| A61K 31/366 | (2006.01) |
| B82Y 40/00 | (2011.01) |
| B82Y 5/00 | (2011.01) |
| B82Y 30/00 | (2011.01) |

(52) U.S. Cl.
CPC .......... *A61K 9/5169* (2013.01); *A61K 31/366* (2013.01); *A61K 47/10* (2013.01); *B82Y 5/00* (2013.01); *B82Y 30/00* (2013.01); *B82Y 40/00* (2013.01)

(58) Field of Classification Search
CPC .... A61K 9/5169; A61K 31/366; A61K 47/10; B82Y 5/00; B82Y 30/00; B82Y 40/00
See application file for complete search history.

(56) References Cited

U.S. PATENT DOCUMENTS

| 9,381,252 B2 | 7/2016 | Agueros Bazo et al. |
| 10,905,651 B1 * | 2/2021 | Murad ............... A61K 49/0008 |
| 2013/0098357 A1 * | 4/2013 | Singh ........................ A61P 5/16 128/200.14 |
| 2013/0116261 A1 * | 5/2013 | Agueros Bazo ........ A61P 39/06 514/249 |
| 2020/0060992 A1 | 2/2020 | Wang |

FOREIGN PATENT DOCUMENTS

WO  WO-2013142279 A1 * 9/2013 ............. A61K 38/08

OTHER PUBLICATIONS

Song et al., "TPGS/Phospholipids Mixed Micelles for Delivery of Icariside II to Multidrug-Resistant Breast Cancer", Integrative Cancer Therapies 2016, vol. 15(3) 390-399.
Tan et al., "Anti-Cancer Properties of the Naturally Occurring Aphrodisiacs: Icariin and Its Derivatives", Front. Pharmacol. (2016) 7:191.
Tang et al., "Enhanced Oral Absorption of Icaritin by Using Mixed Polymeric Micelles Prepared with a Creative Acid-Base Shift Method" Molecules (2021), 26, 3450.
Yang et al., "Pharmacokinetics and tissue distribution profile of icariin propylene glycol-liposome intraperitoneal injection in mice", JPP (2011) 64, 190-198.

* cited by examiner

*Primary Examiner* — Robert A Wax
*Assistant Examiner* — Quanglong N Truong
(74) *Attorney, Agent, or Firm* — WCF IP (57) ABSTRACT

A nano-pharmaceutical formulation, comprising zein nanoparticles, icariin (ICA) or a pharmaceutically acceptable salt thereof encapsulated within the zein nanoparticles, at least one solubilizer, wherein the at least one solubilizer comprises D-a-Tocopherol polyethylene glycol 1000 succinate (TPGS), and one or more pharmaceutical penetration enhancers is provided. Methods of enhancing libido by administering a composition as described herein is also provided.

11 Claims, 9 Drawing Sheets

FIG. 8

ICARIIN NANO-PHARMACEUTICAL FORMULATION

FIELD OF THE INVENTION

The invention is generally related to an icariin nano-pharmaceutical formulation having libido enhancing activity. The formulation comprises naturally derived polymers such as zein nanoparticles.

BACKGROUND OF THE INVENTION

Icariin (ICA) is a prenylated flavonol glycoside and the main active compound of Herba Epimedii [1]. ICA is used as an aphrodisiac, to improve cardiovascular function, as an antirheumatic and in neurodegenerative disorders in traditional Chinese herbal medicine [2-6]. ICA is a diglycoside that is not readily absorbed [7,8]. Despite the wide range of therapeutic efficacy, ICA reduced oral absorption and hence low bioavailability has hindered its clinical application [8,9]. Thus, new formulations for increasing the bioavailability and enhancing the delivery of ICA are needed.

SUMMARY

An aspect of the disclosure provides a composition comprising zein nanoparticles, icariin (ICA) or a pharmaceutically acceptable salt thereof encapsulated within the zein nanoparticles, at least one solubilizer, wherein the at least one solubilizer comprises D-a-Tocopherol polyethylene glycol 1000 succinate (TPGS), and one or more pharmaceutical penetration enhancers. In some embodiments, ICA or the pharmaceutically acceptable salt thereof is present in an amount of 0.4-0.8 wt %. In some embodiments, the zein nanoparticles have an average diameter of 220-230 nm. In some embodiments, the one or more pharmaceutical penetration enhancers are selected from the group consisting of bile salts, terpenes, sulphoxides, azones, alcohols, and alkanols. In some embodiments, the one or more pharmaceutical penetration enhancers comprises sodium deoxycholate. In some embodiments, the composition has a zeta potential of 0.8-1.1 mV.

Another aspect of the disclosure provides a method of enhancing libido in a subject in need thereof, comprising administering an effective amount of a composition as described herein to the subject. In some embodiments, the composition is orally administered. In some embodiments, the subject is male.

DETAILED DESCRIPTION

Embodiments of the disclosure provide nano-pharmaceutical formulations that provide for the enhanced delivery and improved bioavailability of icariin (ICA) or pharmaceutically acceptable salts thereof.

ICA (7-(β-D-Glucopyranosyloxy)-5-hydroxy-4'-methoxy-8-(3-methylbut-2-en-1-yl)-3-(α-L-rhamnopyranosyloxy)flavone) is a prenylated flavonol glycoside, a type of flavonoid. It is the 8-prenyl derivative of kaempferol 3,7-O-diglucoside. The compound has been isolated from several species of plant belonging to the genus *Epimedium* which are commonly known as horny goat weed, Yin Yang Huo, and *Herba epimedii*. Extracts from these plants are reputed to produce aphrodisiac effects, and are used to enhance erectile function. ICA may also protect against atherosclerosis. In some embodiments, ICA or the pharmaceutically acceptable salt thereof is present in an amount of about 0.2-1.0 wt %, e.g. about 0.4-0.8 wt %.

ICA or pharmaceutically acceptable salts thereof may be encapsulated in polymeric nanoparticles to enhance drug delivery. In some embodiments, the nanoparticles are formed from naturally derived polymers, such as zein which is a class of prolamine protein found in maize (corn). Zein nanoparticles are inherently hydrophobic and biodegradable, and therefore, may be used for the controlled release of hydrophobic drugs. In some embodiments, the zein nanoparticles have an average diameter of 220-230 nm. In some embodiments, the zein nanoparticles are present in an amount of about 0.2-1.0 wt %, e.g. about 0.4-0.8 wt %

The compositions of the present disclosure may further comprise at least one solubilizer, such as a tocopherol or tocopherol derivative. Tocopherols are a class of methylated phenols, many of which have vitamin E activity. Tocopherols and their derivatives, such as esters for example, are widely used in vitamin supplementation and as antioxidants in the food industry and in many pharmaceutical compositions. Tocopherols are a range of natural and synthetic compounds, also known by the generic term Vitamin E. α-Tocopherol (chemical name: 2,5,7,8-tetramethyl-2-(4',8', 12'-trimethyldecyl)-6-chromanole) is the most active and widely distributed in nature, and has been the most widely studied. Other members of the class include beta, gamma, and delta tocopherols. Tocopherols occur in a number of isomeric forms, the D and DL forms being the most widely available. As used herein, the term "tocopherol" includes all such natural and synthetic tocopherol or Vitamin E compounds.

Any of the forms or isomers of tocopherols and their derivatives, eg. esters may be used according to the present disclosure. Thus for example, α-tocopherol can be used as such or in the form of its esters such as α-tocopherol acetate, linoleate, nicotinate or hemi succinate-ester, many of which are available commercially.

The tocopherol derivative includes chemical derivatives of vitamin E with ester and ether linkages of various chemical moieties to polyethylene glycol of various lengths. For example, the derivative may include vitamin E tocopherol polyethylene glycol succinate derivatives with PEG molecular weights between about 500 and 6000 Da. In some embodiments, the vitamin E polymeric derivative is D-α-Tocopherol polyethylene glycol 1000 succinate (TPGS). In an embodiment, the solubilizer is present in the composition from about 2 wt % to about 8 wt %/volume, e.g. about 4-6 wt %. It should be understood that throughout the specification the term weight percent (wt %) refers to mass per unit volume, unless otherwise specified.

TPGS is a water soluble derivative of Vitamin E in which polyethylene glycol subunits are attached by a succinic acid diester at the ring hydroxyl of the vitamin E molecule. TPGS is an almost odourless waxy amphiphilic substance with a molecular weight about 1513.

The tocopherol solubilizer of the disclosure may be used alone or in conjunction with other known surfactants eg. phospholipids, polysorbates, sorbitan esters of fatty acids, cetearyl glucoside or poloxamers or other stabilisers such as xanthan gum, or propylene glycol alginate. In some embodiments, the surfactant comprises polyethylene glycol (PEG) of various molecular weights, such as PEG 200. In an embodiment, the additional surfactant is present in the composition from about 2 wt % to about 8 wt %/volume, e.g. about 4-6 wt %.

The compositions of the present disclosure may further comprise one or more pharmaceutical penetration enhancers, such as one or more of bile salts, terpenes, sulphoxides, azones, alcohols, and alkanol. Bile salts are composed of the salts of four different kinds of free bile acids (cholic, deoxycholic, chenodeoxycholic, and lithocholic acids); each of these acids may in turn combine with glycine or taurine to form more complex acids and salts. Bile salts have membrande destabilizing activity. In some embodiments, the bile salt is sodium deoxycholate (SDC). In some embodiments, the penetration enhancer is present in an amount of about 0.1-0.5 wt %, e.g. about 0.2-0.4 wt %.

The compositions of the present disclosure may also contain other components such as, but not limited to, additives, adjuvants, buffers, tonicity agents, bioadhesive polymers, and preservatives. In any of the compositions of this disclosure, the mixtures are preferably formulated at about pH 5 to about pH 8. This pH range may be achieved by the addition of buffers to the composition. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose.

In an embodiment, compositions of the present disclosure further comprise one or more bioadhesive polymers. Bioadhesion refers to the ability of certain synthetic and biological macromolecules and hydrocolloids to adhere to biological tissues. Bioadhesion is a complex phenomenon, depending in part upon the properties of polymers, biological tissue, and the surrounding environment. Several factors have been found to contribute to a polymer's bioadhesive capacity: the presence of functional groups able to form hydrogen bridges (—OH, COOH), the presence and strength of anionic charges, sufficient elasticity for the polymeric chains to interpenetrate the mucous layer, and high molecular weight.

In an embodiment, a composition of the present disclosure includes at least one bioadhesive polymer. Bioadhesive polymers of the present disclosure include, for example, carboxylic polymers like Carbopol® (carbomers), Noveon® (polycarbophils), cellulose derivatives including alkyl and hydroxyalkyl cellulose like methylcellulose, hydroxypropylcellulose, carboxymethylcellulose, gums like locust beam, xanthan, agarose, karaya, guar, and other polymers including but not limited to polyvinyl alcohol, polyvinyl pyrollidone, polyethylene glycol, Pluronic® (Poloxamers), tragacanth, and hyaluronic acid; phase-transition polymers for providing sustained and controlled delivery of enclosed medicaments to the eye (e.g., alginic acid, carrageenans (e.g., Eucheuma), xanthan and locust bean gum mixtures, pectins, cellulose acetate phthalate, alkylhydroxyalkyl cellulose and derivatives thereof, hydroxyalkylated polyacrylic acids and derivatives thereof, poloxamers and their derivatives, etc. Physical characteristics in these polymers can be mediated by changes in environmental factors such as ionic strength, pH, or temperature alone or in combination with other factors. In an embodiment, the optional one or more bioadhesive polymers is present in the composition from about 0.01 wt % to about 10 wt %/volume, preferably from about 0.1 to about 5 wt %/volume. In an embodiment, the compositions of the present disclosure further comprise at least one hydrophilic polymer excipient selected from, for example, PVP-K-30, PVP-K-90, HPMC, HEC, and polycarbophil.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

The active ingredients may be mixed with excipients which are pharmaceutically acceptable and compatible with the active ingredients. "Pharmaceutically" or "pharmaceutically acceptable" refer to molecular entities and compositions that do not produce an adverse, allergic or other untoward reaction when administered to a mammal, e.g. a human, as appropriate. A pharmaceutically acceptable carrier or excipient refers to a non-toxic solid, semi-solid or liquid filler, diluent, encapsulating material or formulation auxiliary of any type. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of the compounds in the formulations may vary. However, in general, the amount in the formulations will be from about 0.01-99%, weight/volume.

A solvate is the result of solvation which is an interaction of a solute (i.e. compound of the disclosure) with a solvent. Solvation leads to stabilization of the solute species in the solution. A solvate refers to the solvated state, whereby an ion in a solution is surrounded or complexed by solvent molecules. Exemplary solvents include, but are not limited to, propylene glycol; polypropylene glycol; polyethylene glycol (for example, polyethylene glycol 300, polyethylene glycol 400, polyethylene glycol 600, polyethylene glycol 900, polyethylene glycol 540 (all available from Union Carbide) and the like); pharmaceutically acceptable alcohols (for example, ethanol or 2-(2-ethoxyethoxy)ethanol (Transcutol®, Gattefosse, Westwood, N.J. 07675) and the like); polyoxyethylene castor oil derivatives (for example, polyoxyethyleneglycerol triricinoleate or polyoxyl 35 castor oil (Cremophor®EL, BASF Corp.), polyoxyethyleneglycerol oxystearate (Cremophor®RH 40 (polyethyleneglycol 40 hydrogenated castor oil) or Cremophor®RH 60 (polyethyleneglycol 60 hydrogenated castor oil), BASF Corp.) and the like); fractionated coconut oil (for example, mixed triglycerides with caprylic acid and capric acid (Miglyol®812, available from Huls AG, Witten, Germany) and the like); Tween®80; isopropyl palmitate; isopropyl myristate; pharmaceutically acceptable silicon fluids; and the like.

"Salts" or "pharmaceutically acceptable salts" refers to the relatively non-toxic, inorganic and organic acid addition salts, and base addition salts, of compounds of the present disclosure. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

Compositions as described herein may be prepared either as liquid solutions or suspensions, or as solid forms such as tablets, pills, granules, capsules, powders, ampoules, and the like. The liquid may be an aqueous liquid. Solid forms suitable for solution in, or suspension in, liquids prior to administration may also be prepared.

Whilst the beneficial effects of the disclosure are particularly apparent in oral delivery, the utility of the disclosure is not limited and the formulations according to the invention may also be administered parenterally or enterally, eg. as implants or by intravenous, intramuscular or subcutaneous injection, or by infusion.

The present disclosure also provides a method of treatment of a human or non-human animal subject by delivery of a substantially insoluble or sparingly soluble biologically active agent, said method comprising administering to said subject a formulation as described herein, with or without an additional biological active agent. The compositions and dosage forms of the disclosure may be useful for the treatment of any disease or disorder that the included active agent is useful for treating. In some embodiments, the disclosure provides methods for enhancing the libido of a subject. In some embodiments, the composition or dosage form may be useful for the treatment of cardiovascular disorders or erectile dysfunction.

A patient or subject to be treated by any of the compositions or methods of the present disclosure can mean either a human or a non-human animal including, but not limited to, dogs, horses, cats, rabbits, gerbils, hamsters, rodents, birds, aquatic mammals, cattle, pigs, camelids, and other zoological animals.

In some embodiments, the formulation or active agent is administered to the subject in a therapeutically effective amount. By a "therapeutically effective amount" or an "effective amount" is meant a sufficient amount to treat the disease or disorder at a reasonable benefit/risk ratio applicable to any medical treatment. It will be understood that the total daily usage of the compositions of the present disclosure will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Embodiments of the disclosure also provide methods of preparing a composition as described herein. For example, ICA-tocozeinolate nanospheres may be prepared by dissolving specified amounts of ICA and TPGS in absolute ethanol. A specified amount of zein may be dissolved in 90% ethanol. Both alcoholic solutions are mixed under stirring. SDC may be dissolved in distilled water. The aqueous solution may then be mixed with the alcoholic solution under stirring and then subjected to rotary evaporation at 30-40° C. until complete evaporation of the alcoholic part. The prepared solution may then be centrifuged, washed, and then subjected to lyophilization.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

Icariin (ICA) is the main active compound of *Epimedium* genus that is used as aphrodisiac in traditional Chinese herbal medicine. Despite ICA therapeutic efficacy, ICA reduced oral absorption and hence low bioavailability hindered its clinical application. In this study, a novel tocozeinolate nanosphere formula was designed aiming to improve drug efficacy. The ICA-tocozeinolate nanosphere formula was optimized using D-optimal response surface experimental design. The concentration of ICA (X1), D-α-Tocopherol polyethylene glycol 1000 succinate (TPGS, X2), Zein (X3), and Sodium deoxycholate (SDC, X4) expressed as percentages were investigated as quantitative independent variables. The design generated 23 formulas that were investigated for particle size (PS, nm), zeta potential (ZP, mV), and entrapment efficiency (EE, %) that were selected as response parameters. Numerical optimization and the desirability approach were implemented to predict the optimized variables' levels that, upon combination, could result in minimized size and maximized both zeta potential and ICA entrapment. Sexual behavior of optimized ICA-tocozeinolate nanospheres was investigated in male rats. The optimized ICA-tocozeinolate nanospheres showed particle size of 224.45 nm, zeta potential of 0.961 mV, and drug entrapment of 65.29% that coincide well with the predicted values. The optimized ICA-tocozeinolate nanospheres resulted in an enhancement of male rat sexual behavior as compared to raw ICA at equivalent doses (20 mg/kg). This was evidenced by decreased average time of both Mount latency (ML) and ejaculation latency (EL) to almost half that of raw ICA. Also, intromission latency (IL) time was reduced by 41% when compared to the raw ICA. These results revealed that optimized ICA-tocozeinolate nanospheres improve the delivery and efficacy of therapeutic agents.

Methods

Materials

Icariin, zein, TPGS and SDC were purchased from Sigma-Aldrich Burlington, Mass., United States.

Experimental Design and Optimization of ICA-Tocozeinolate Nanospheres

The ICA-tocozeinolate nanosphere formula was optimized using D-optimal response surface experimental design. The concentration of ICA ($X_1$), TPGS ($X_2$), Zein ($X_3$), and SDC ($X_4$) expressed as percentages were investigated as quantitative independent variables. The upper and lower coded and actual levels of the four variables are compiled in Table 1. Particle size (PS, nm, $Y_1$), zeta potential (ZP, mV, $Y_2$), and entrapment efficiency (EE, %, $Y_3$) were selected as response parameters. As per the selected design, 23 experimental runs, including three lack of fit points, four replicate points, and additional center point were generated by Design-Expert software (Version 12; Stat-Ease Inc., Minneapolis, Minn., USA); the combination of variables' levels for each experimental run is listed in Table 2. The optimal model fitting the data of each response was selected amongst linear, two-factor interaction (2FI), and quadratic models based on the computed predicted and adjusted determination coefficients ($R^2$) as well as adequate precision. The goodness of data fitting was assessed using the diagnostic plots generated by the software. The terms' coefficients in the equations expressing the best fitting model for each response were utilized to predict the relative magnitude of the corresponding variable or interaction impact. Analysis of variance (ANOVA) was applied for statistical analysis of the responses to estimate the significance of the studied variables and the interaction between them at $P<0.05$. The effect of the investigated variables and the interaction between them were graphically illustrated using two-dimensional contour and three-dimensional response surface plots. Numerical optimization and desirability approach was applied on the measured data to predict the optimal variables' levels that could achieve the desired set goals for the responses upon combination, Table 1.

TABLE 1

Factor levels (coded and actual) and response desirability constraints in the response surface D-optimal design used for optimization of ICA-tocozeinolate nanospheres

| Factors | Levels | | |
|---|---|---|---|
| | −1 | 0 | +1 |
| X1: ICA conc (% w/v) | 0.4 | 0.6 | 0.8 |
| X2: TPGS concentration (% w/v) | 4 | 5 | 6 |
| X3: Zein Concentration (% w/v) | 0.4 | 0.6 | 0.8 |
| X4: SDC concentration (% w/v) | 0.2 | 0.3 | 0.4 |

| Responses | Desirability constraints |
|---|---|
| Y1: Particle size (nm) | Minimize |
| Y2: Zeta potential (mV) | Maximize |
| Y3: Entrapment efficiency % | Maximize |

Abbreviations:
ICA, Icariin;
TPGS, D-a-tocophelyl polyethylene glycol 1000 succinate;
SDC, sodium deoxycholate

TABLE 2

Combination of independent variables' levels in ICA-tocozeinolate nanospheres experimental runs and their corresponding responses.

| | Independent Variables | | | | Dependent Variables | | |
|---|---|---|---|---|---|---|---|
| | | | | | PS* ± | ZP* ± | EE* ± |
| RUN | ICA concentration ($X_1$, % w/v) | TPGS concentration (X2, % w/v) | Zein concentration ($X_3$, % w/v) | SDC concentration ($X_4$, % w/v) | SD ($Y_1$, nm) | SD ($Y_2$, mV) | SD ($Y_2$, %) |
| 1 | 0.40 | 4.00 | 0.80 | 0.40 | 188.2 ± 18.6 | −7.36 ± 1.3 | 61.2 ± 5.2 |
| 2 | 0.80 | 4.00 | 0.80 | 0.40 | 259.6 ± 20.1 | −6.83 ± 0.7 | 72.1 ± 6.7 |
| 3 | 0.80 | 4.00 | 0.80 | 0.20 | 421.3 ± 29.3 | +0.96 ± 0.1 | 78.5 ± 4.3 |
| 4 | 0.60 | 5.00 | 0.60 | 0.30 | 279.2 ± 24.2 | −4.13 ± 0.5 | 60.3 ± 7.2 |
| 5 | 0.80 | 5.33 | 0.80 | 0.27 | 303.1 ± 25.7 | −1.95 ± 0.1 | 69.4 ± 3.5 |
| 6 | 0.80 | 6.00 | 0.60 | 0.20 | 333.6 ± 27.1 | −0.63 ± 0.1 | 65.7 ± 5.8 |
| 7 | 0.60 | 4.00 | 0.40 | 0.20 | 538.7 ± 37.4 | −0.21 ± 0.03 | 63.3 ± 3.1 |
| 8 | 0.80 | 4.00 | 0.40 | 0.40 | 329.8 ± 26.2 | −9.91 ± 0.8 | 63.6 ± 6.9 |
| 9 | 0.80 | 6.00 | 0.60 | 0.20 | 328.4 ± 29.7 | −0.71 ± 0.2 | 64.9 ± 8.1 |
| 10 | 0.40 | 5.00 | 0.80 | 0.20 | 268.1 ± 26.5 | +1.94 ± 0.2 | 62.8 ± 5.2 |
| 11 | 0.60 | 6.00 | 0.80 | 0.20 | 242.4 ± 19.4 | +2.33 ± 0.1 | 64.1 ± 4.6 |
| 12 | 0.80 | 4.67 | 0.40 | 0.20 | 494.9 ± 31.6 | −1.31 ± 0.1 | 68.5 ± 5.1 |
| 13 | 0.40 | 5.00 | 0.40 | 0.40 | 203.1 ± 23.7 | −11.63 ± 0.9 | 36.2 ± 3.1 |
| 14 | 0.40 | 6.00 | 0.80 | 0.30 | 139.6 ± 16.9 | −6.15 ± 0.5 | 51.7 ± 3.1 |

TABLE 2-continued

Combination of independent variables' levels in ICA-tocozeinolate nanospheres experimental runs and their corresponding responses.

| | Independent Variables | | | | Dependent Variables | | |
|---|---|---|---|---|---|---|---|
| | | | | | PS* ± | ZP* ± | EE* ± |
| RUN | ICA concentration ($X_1$, % w/v) | TPGS concentration (X2, % w/v) | Zein concentration ($X_3$, % w/v) | SDC concentration ($X_4$, % w/v) | SD ($Y_1$, nm) | SD ($Y_2$, mV) | SD ($Y_2$, %) |
| 15 | 0.80 | 4.00 | 0.40 | 0.40 | 334.3 ± 21.4 | −10.45 ± 0.9 | 63.9 ± 2.9 |
| 16 | 0.40 | 6.00 | 0.60 | 0.40 | 114.2 ± 15.4 | −8.41 ± 0.6 | 35.8 ± 2.1 |
| 17 | 0.80 | 6.00 | 0.40 | 0.40 | 221.4 ± 31.2 | −13.27 ± 1.1 | 57.9 ± 4.4 |
| 18 | 0.80 | 6.00 | 0.80 | 0.40 | 148.7 ± 23.1 | −7.83 ± 0.3 | 64.4 ± 5.1 |
| 19 | 0.67 | 6.00 | 0.40 | 0.27 | 311.8 ± 35.2 | −4.82 ± 0.3 | 58.8 ± 6.1 |
| 20 | 0.40 | 4.00 | 0.80 | 0.40 | 194.9 ± 24.7 | −6.97 ± 0.4 | 60.5 ± 7.1 |
| 21 | 0.80 | 4.00 | 0.80 | 0.20 | 406.2 ± 54.3 | +0.35 ± 0.03 | 76.9 ± 5.2 |
| 22 | 0.40 | 6.00 | 0.40 | 0.20 | 291.2 ± 17.5 | −2.61 ± 3.6 | 44.2 ± 3.1 |
| 23 | 0.40 | 4.00 | 0.40 | 0.27 | 364.3 ± 22.1 | −3.44 ± 2.7 | 55.1 ± 4.8 |

Abbreviations:
ICA, Icariin;
TPGS, D-α-tocopheryl polyethylene glycol 1000 succinate;
SDC, sodium deoxycholate
PS, particle size;
ZP, zeta potential;
EE%, entrapment efficiency.

Preparation of ICA-Tocozeinolate Nanospheres

The preparation of ICA-tocozeinolate nanospheres was carried out by dissolving specified amounts of ICA and TPGS (according to the experimental design) in absolute ethanol (25 mL). Specified amounts of zein by the design were dissolved in 90% ethanol. Both alcoholic solutions were mixed under stirring. SDC (specified amounts) was dissolved in distilled water. The aqueous solution was then mixed with the alcoholic solution under stirring. The prepared solution was kept stirring for 30 min. After that the solution was subjected to rotary evaporation at 35° C. till complete evaporation of the alcoholic part. The prepared solution was centrifuged at 20,000 rpm and washed twice then subjected to lyophilization.

In Vivo Investigation

Sexual Behavior of Optimized ICA-Tocozeinolate Nanospheres

Wistar rats (210-240 g) of both sexes were obtained from the animal facility, King Abdulaziz University (KAU). Animals were housed, females and males, separately in the animal facility at 12-hour light-dark cycle and a temperature of 22±2° C. They were provided with pellet diet and water ad libitum. The animals were acclimatized to the housing environment for 7 days before dosing. The animal care procedures were certified by Faculty of Pharmacy's Research Ethics Committee. Sexual behavior of males was observed by well-trained technicians, without knowing the study protocol, in an air conditioned, sound-attenuated room lit with a faint red light, amid the first period of the dark cycle of day 10. Single male rats were transferred into rectangular glass monitoring cages (40×50×40 cm) and allowed to get accommodated to the testing chamber for 15 min. Then, sexually receptive female rats were presented in the cages (1 female per cage) and the mating test began.

Parameters of sexual behavior were assessed as beforehand explained [20][21]. Mount latency (ML) is defined as time (in seconds) from the introduction of the female to the first mount; ejaculation latency (EL) is defined as time (in seconds) from the first intromission to ejaculation; and intromission latency (IL) is defined as time (in seconds) from introduction of the female to the first intromission (vaginal penetration).

Results and Discussion

Experimental Design and Fit Statistics

Fit statistical analysis results for the responses, namely, vesicle size, zeta potential, and entrapment efficiency are presented in Table 3. On the basis of the highest $R^2$ and lowest PRESS, the vesicle size data fitted the 2FI model; the zeta potential fitted the linear model, while the entrapment efficiency fitted the quadratic model. The adjusted $R^2$ and the predicted $R^2$ for each response exhibited appropriate coincidence with difference of less than the permissible limit of 0.2 verifying the model validity. Moreover, the selected model for each response exhibited adequate precision value greater than the desirable value of 4 indicating appropriate signal to noise ratio. According to the previously computed parameters, the selected models could be adequately utilized to explore the experimental design space.

The goodness of fit of the selected models was further verified via developing diagnostic plots illustrated in FIG. 1. The points in the externally studentized residuals vs. run plots, FIGS. 1 (A, C, and E) were scattered randomly within the limits (illustrated by the lines) indicating the absence of any lurking variable that could exert an influence on any of the measured responses. Moreover, the predicted versus actual plots, illustrated in FIGS. 1 (B, D, and F) showed highly linear pattern revealing that the observed responses showed good analogy to the predicted ones [16,22]

TABLE 3

Fit statistics of ICA-tocozeinolate nanospheres' responses according to the best fitting model.

| Responses | Model | Sequential P-value | Lack of fit P-value | $R^2$ | Adjusted $R^2$ | Predicted $R^2$ | Adequate precision | PRESS |
|---|---|---|---|---|---|---|---|---|
| $Y_1$: PS (nm) | 2FI | 0.0036 | 0.1138 | 0.9947 | 0.9903 | 0.9806 | 53.77 | 4845.41 |
| $Y_2$: ZP (mV) | Linear | <0.0001 | 0.1582 | 0.9733 | 0.9673 | 0.9563 | 34.61 | 17.99 |
| $Y_3$: EE (%) | Quadratic | 0.0030 | 0.2436 | 0.9977 | 0.9937 | 0.9772 | 59.88 | 58.20 |

Abbreviations:
ICA, Icariin;
PS, particle size;
ZP, zeta potential;
EE%, entrapment efficiency;
2FI, Two-factor interaction;
PRESS, predicted residual error sum of squares.

Influence of Variables on Particle Size

Invading malignant tumor tissues is regarded as a major challenge in the formulation of actives with anticancer activity. This necessitates the need of continuous research to manipulate the drug delivery systems characteristics aiming at enhancing tumor accessibility [23]. Nanoparticulate systems with a size less than 400 nm have recently attracted attention in the arena of malignancy therapy owing to preferential distribution within solid cancerous masses [24, 25]. The prepared optimized ICA-tocozeinolate nanospheres exhibited promising sizes that ranged from 114.2±15.4 to 538.7±37.4 nm. Despite this finding, it is reported that the preferential buildup of nano-sized delivery system and its corresponding therapeutic efficacy might be overcome by inefficacious tumor tissue entry that could result from the pathological status created by the malignancy growth [26]. Tumor penetration enhancement could be verified through reducing size to its possible minimum value to enhance the surface area available for penetrating the tissues [27]. Thus, the study aimed at optimizing the nanospheres to a minimized size. Analysis of variance (ANOVA) for size confirmed the significance of the 2FI model as evidenced by the F-value of 225.57 (P<0.0001). The lack of fit F-value of 3.64 (P=0.1138) shows a non-significant lack of fit; thus, fitting of the measured size to the recommended model is ensured. The equation demonstrating the 2FI model in terms of coded factor was generated by the software as follows:

$$Y_1 \text{ (particle size)} = 286.02 + 40.15X_1 - 64.99X_2 - 45.04X_3 - 80.35X_4 + 1.61X_1X_2 - 2.69X_1X_3 - 4.20X_1X_4 + 4.82X_2X_3 + 10.38X_2X_4 + 12.70X_3X_4$$

Figure 1A:
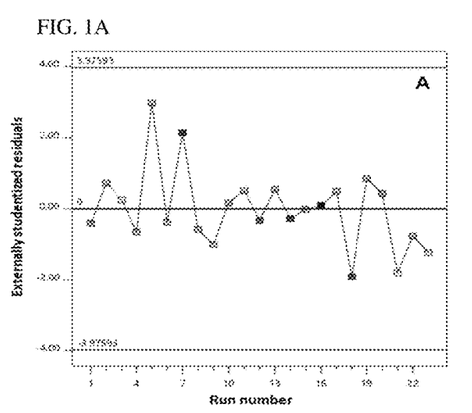
FIGS. 1A-F. Diagnostic plots for particle size (A, B), zeta potential (C, D), and entrapment efficiency (E, F) for the measured responses of ICA-tocozeinolate nanospheres. Externally studentized residuals vs. run number plot (A, C, E) and normal probability plot (B, D, F).
Figure 1B:
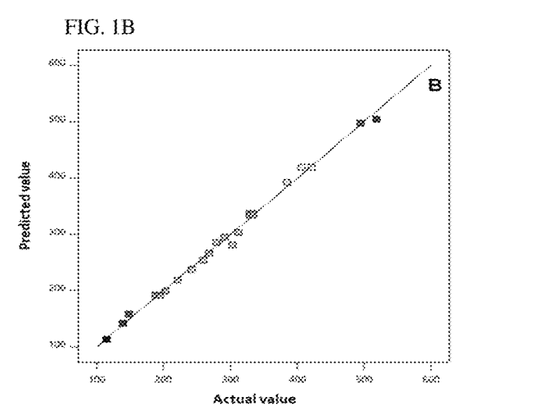
Figure 1C:
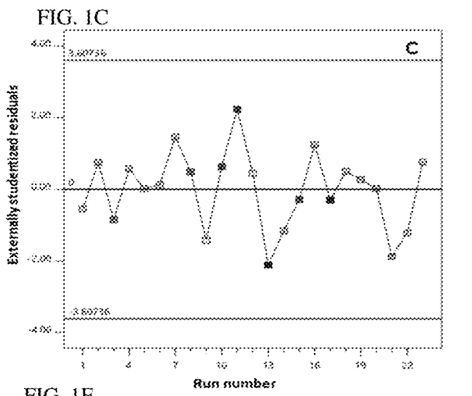
Figure 1D:
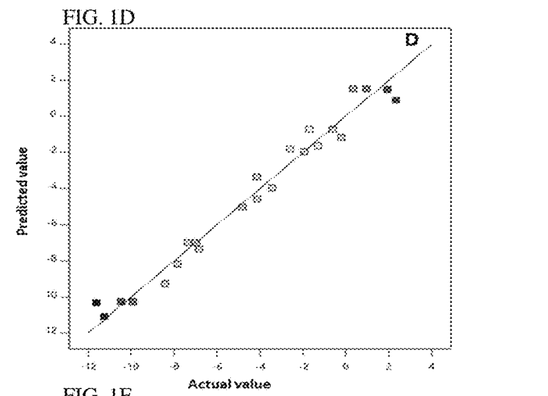
Figure 1E:
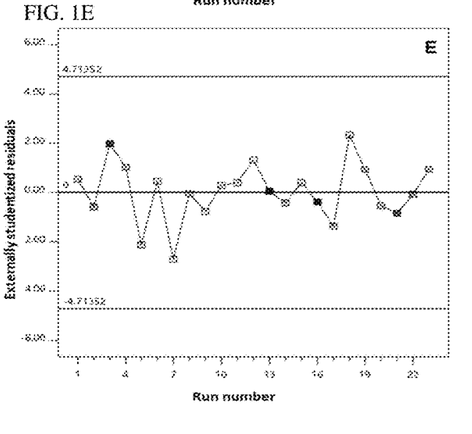
Figure 1F:
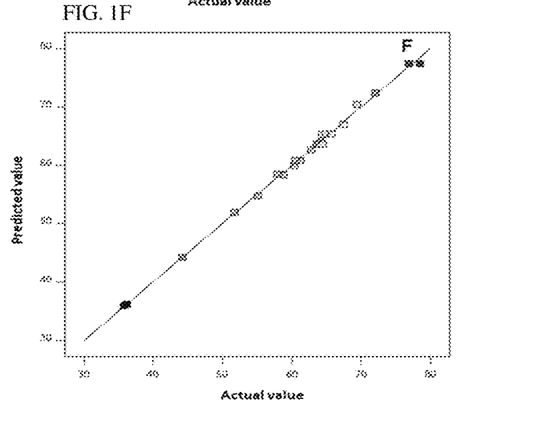
Figure 2A:
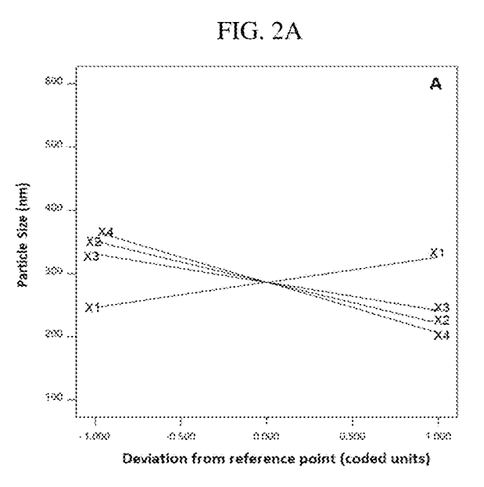
FIGS. 2A-C. Perturbation graph for the main effects of critical attributes: ICA concentration ($X_1$), TPGS concentration ($X_2$), Zein concentration ($X_3$), and SDC concentration ($X_4$) on (A) particle size, (B) zeta potential, and (C) entrapment efficiency of ICA-tocozeinolate nanospheres.

The statistical analysis revealed that all the linear terms corresponding to the four investigated variables had a significant effect on size (P<0.0001 for all terms). The interaction terms $X_2X_4$ and $X_3X_4$ representing the interaction between SDC concentration and either TPGS or zein concentrations, respectively were also found to be significant at P<0.05. FIG. 2A illustrates the perturbation graph demonstrating the impact of the studied factors on size, while FIG. 3 illustrates the 3D-response and the 2D-contour plots that demonstrate the interaction between the significant variables. The illustrations show that the nanosphere size significantly increases with increasing ICA concentration, while decreases with increasing TPGS, zein, and SDC concentrations. This finding is supported by the positive sign of $X^1$ coefficient and the negative sign of $X_2$, $X_3$, and $X_4$ coefficients. The order of significance was SDC>TPGS>Zein>ICA as evidenced by the values of the linear terms' coefficients in the developed equation. The increase in the size at higher drug concentrations was reported in previous studies [28]. The direct relationship between ICA concentration and size could be related to the increased entrapment of the lipophilic compound in the developed nanospheres [29]. The reduced size observed at higher SDC concentrations might be attributed to the stabilizing effect of SDC on colloidal nanospheres dispersion with consequent aggregation reduction [30].

Influence of Variables on Zeta Potential

Zeta potential value is related to the type and magnitude of the surface charge of nanoparticles. The prepared ICA-tocozeinolate nanospheres exhibited zeta potential values ranging from −11.63±3.4 to 2.33±2.4 mV. It is documented that positively charged nanoparticles could have better permeation ability and accumulation within cancerous tissues and tumor vasculature in comparison to the surrounding environment [31-33]. Therefore, the prepared nanospheres were optimized to maximize the zeta potential value.

Analysis of variance (ANOVA) for zeta potential confirmed the significance of the linear model as depicted by the corresponding F-value of 163.92 (P<0.0001), respectively. The lack of fit F-value of 2.88 (P=0.1582) reflects non-significant lack of fit; thus, the fitting of zeta potential values to the proposed model is confirmed. The software was employed to develop the equation demonstrating the linear model for the zeta potential in terms of coded factor as follows:

$$Y_2 \text{ (zeta potential)} = -4.58 - 0.1813X_1 - 0.4082X_2 + 1.45X_3 - 4.45X_4$$

Figure 2B:
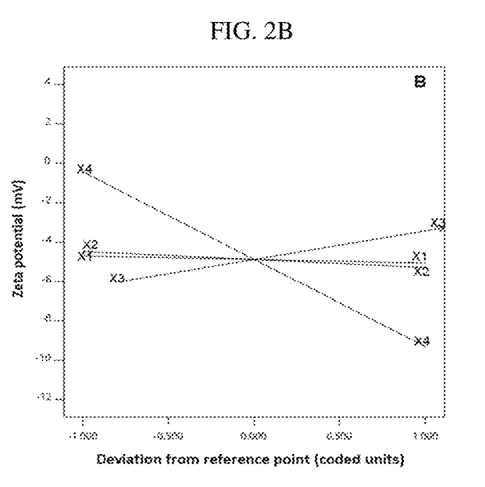

The statistical analysis revealed that the linear terms $X_2$, $X_3$, and $X_4$ corresponding to concentration of TPGS, zein, and SDC exhibited a significant effect on zeta potential (P=0.041 for $X_2$ and P<0.0001 for $X_3$ and $X_4$). The extremely lower P value of the coefficient of $X_3$ and $X_4$ reveals that zein and SDC concentrations play an important role on the zeta potential value. Further, SDC concentration possessed the highest impact as evidenced by the highest coefficient of the term $X_4$. FIG. 2B illustrates the perturbation graph demonstrating the main effects of the studied factors on the zeta potential. The illustration shows that the zeta potential significantly increases at higher zein concentration and lower TPGS and SDC concentrations. The positive sign of $X_3$ and the negative signs of $X_2$ and $X_4$ coefficients supports this observation. The SD concentration was the most prominent effect on the zeta potential as depicted by the highest corresponding linear term coefficient in the equation. The decreased zeta potential at higher SDC concentrations could be explained by the possible binding between the anionic head groups of SDC with the cationic amino acid moieties of zein protein, which would could cause a marked exposure of the anionic residues [30,34].

Influence of Variables on Entrapment Efficiency

The prepared ICA-tocozeinolate nanospheres exhibited wide variation in entrapment efficiency ranging from 44.2±7.1 to 78.5±4.3%. Aiming at maximizing ICA entrapment, the influence of formulation factors on entrapment efficiency was studied.

Analysis of variance (ANOVA) for entrapment efficiency provided further proof for the significance of the quadratic model as evidenced by the F-value of 247.38 (P<0.0001). The lack of fit F-value of 2.11 (P=0.2436) shows a non-significant lack of fit; thus, assuring the fitting of the entrapment efficiency data to the recommended model was accomplished. The equation demonstrating the quadratic model in terms of coded factor was generated by the software as follows:

$$Y_3 \text{ (entrapment efficiency)} = 59.92 + 8.08X_1 - 5.47X_2 + 5.01X_3 - 4.56X_4 + 2.02X_1X_2 - 1.94X_1X_3 + 1.66X_1X_4 - 0.89X_2X_3 - 0.047X_2X_4 + 0.34X_3X_4 - 1.59X_1^2 + 1.48X_2^2 + 1.52X_3^2 - 1.98X_4^2$$

Figure 2C:
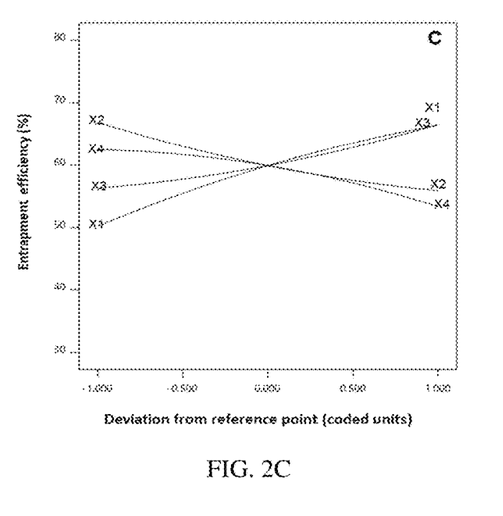
Figure 3A:
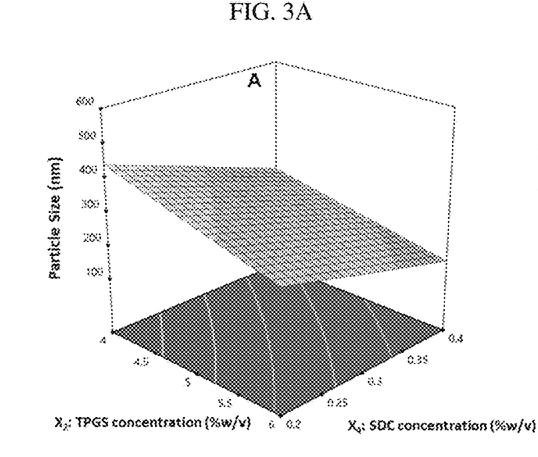
FIGS. 3A-D. Response surface 3D- (A, B) and contour 2D-plots (C, D) showing the interaction between the significant factors on the vesicle size of ICA-tocozeinolate nanospheres.
Figure 3B:
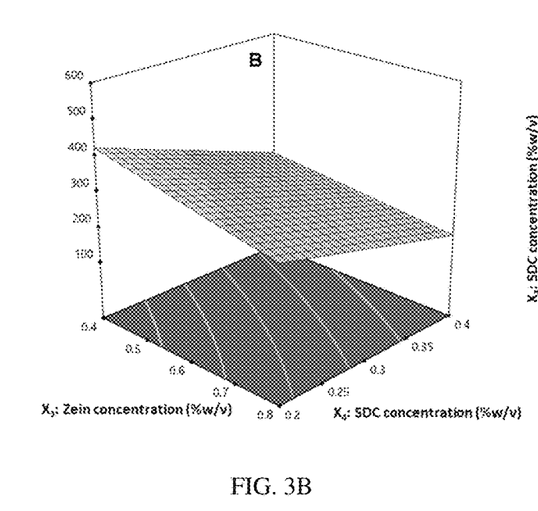
Figure 3C:
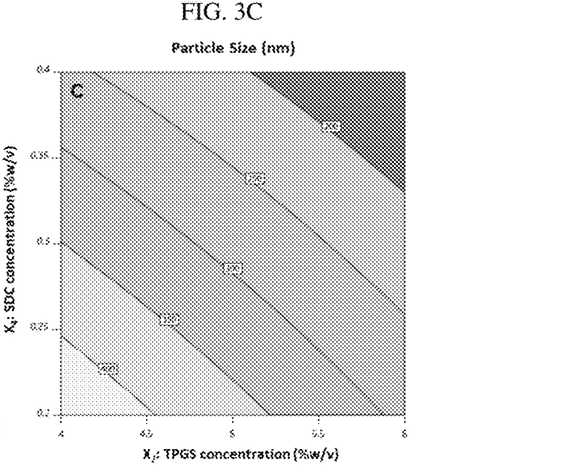
Figure 3D:
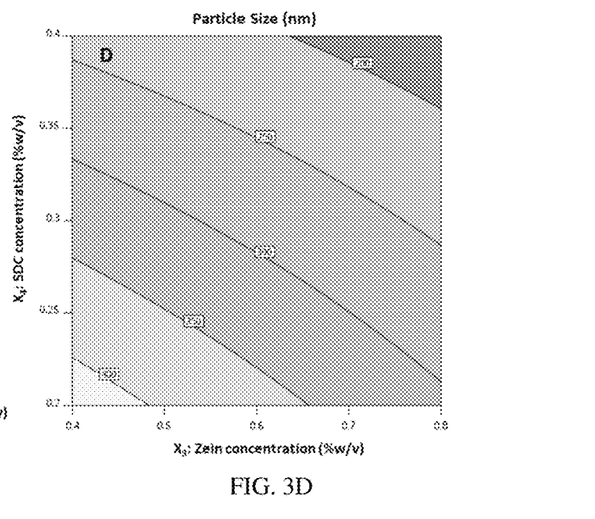
Figure 4A:
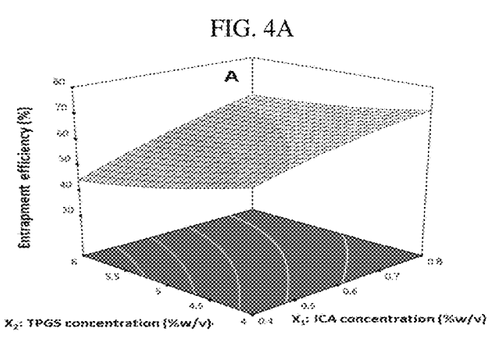
FIGS. 4A-H. Response surface 3D- (A, B, C, D) and contour 2D-plots (E, F, G, H) showing the interaction between the significant factors on the entrapment efficiency of ICA-tocozeinolate nanospheres.
Figure 4B:
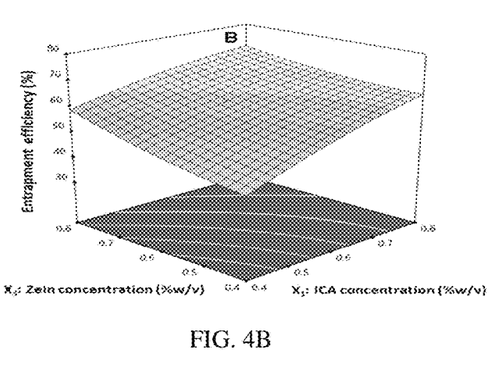
Figure 4C:
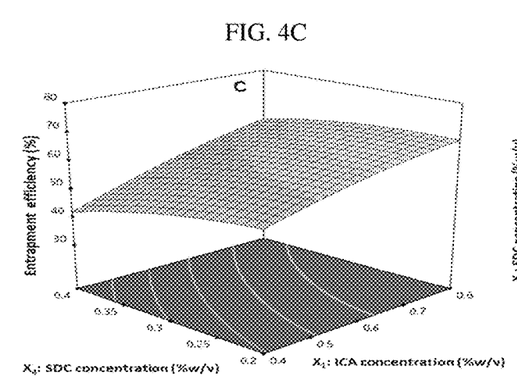
Figure 4D:
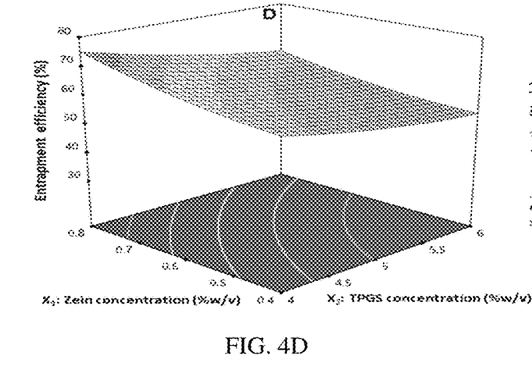
Figure 4E:
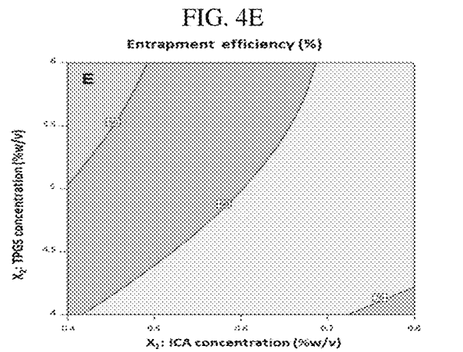
Figure 4F:
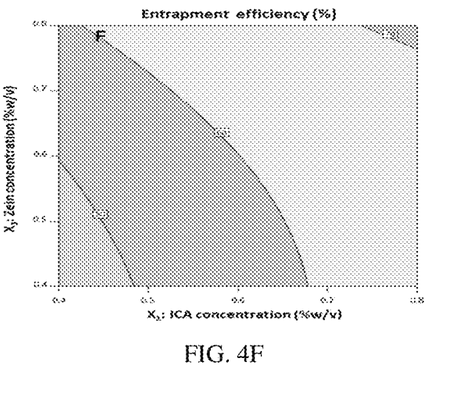
Figure 4G:
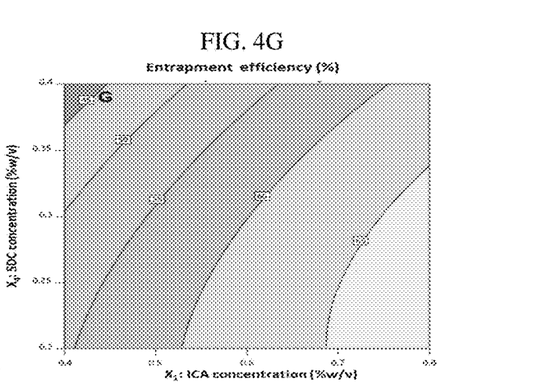
Figure 4H:
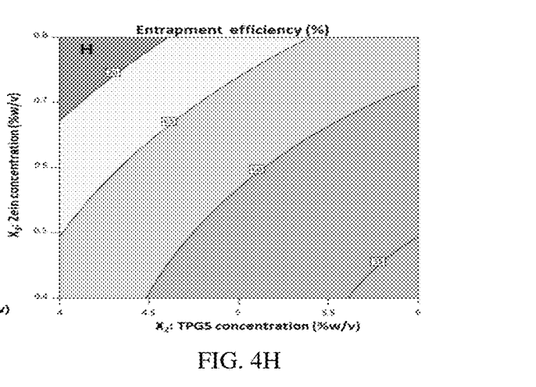

ANOVA results revealed that all the linear terms and the quadratic terms corresponding to the four investigated variables exhibited a markedly significant impact on entrapment efficiency (P<0.0001 for all linear terms; P=0.0192, 0.0160, 0.0314, and 0.0053 for $X_1^2$, $X_2^2$, $X_3^2$, and $X_4^2$, respectively). The interaction terms $X_1X_2$, $X_1X_3$, $X_1X_4$, and $X_2X_3$ representing the interaction between ICA concentration and either TPGS, zein, or SDC concentration and the interaction between TPGS and zein concentrations, respectively were also found to be significant at P<0.05. FIG. 2C illustrates the perturbation graph demonstrating the impact of the studied factors on entrapment, while FIG. 4 illustrates the 3D-response and the 2D-contour plots that represent the interaction between the significant variables. The illustrations shows that ICA entrapment significantly increases with increasing ICA and zein concentrations, while decreases with increasing TPGS and SDC concentrations. This finding is supported by the positive sign of $X_1$ and $X_3$ coefficients and the negative sign of $X_2$ and $X_4$ coefficients. The higher retention of ICA at higher zein and ICA concentrations might be credited to the hydrophobic interactions between the lipophilic compound and the apolar groups of zein. Previous studies demonstrated significant lipophilic moieties entrapment within zein nano-sized systems [12,35].

Optimization of ICA-Tocozeinolate Nanospheres

Figure 5A:
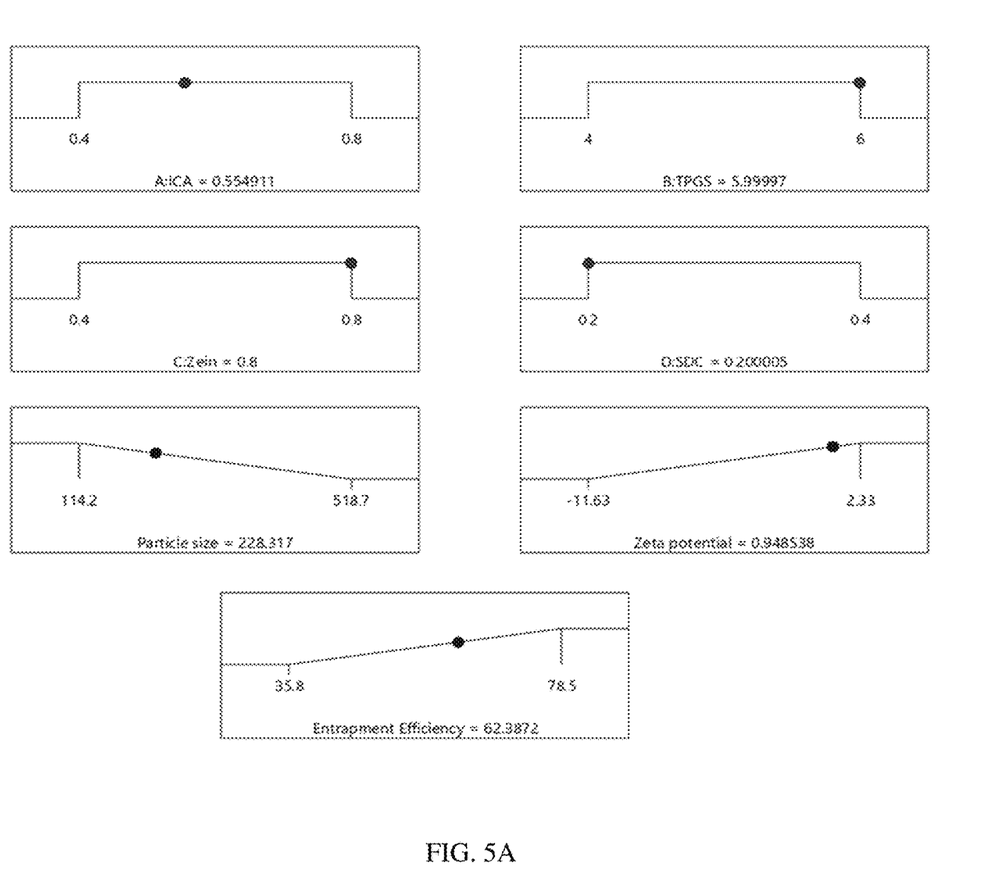
FIGS. 5A-B. (A) Ramp graphs representing the optimized levels of the independent variables and the predicted responses for the optimized ICA-tocozeinolate nanospheres. (B) Desirability values for the predicted responses and overall desirability of the optimized ICA-tocozeinolate nanospheres.
Figure 5B:
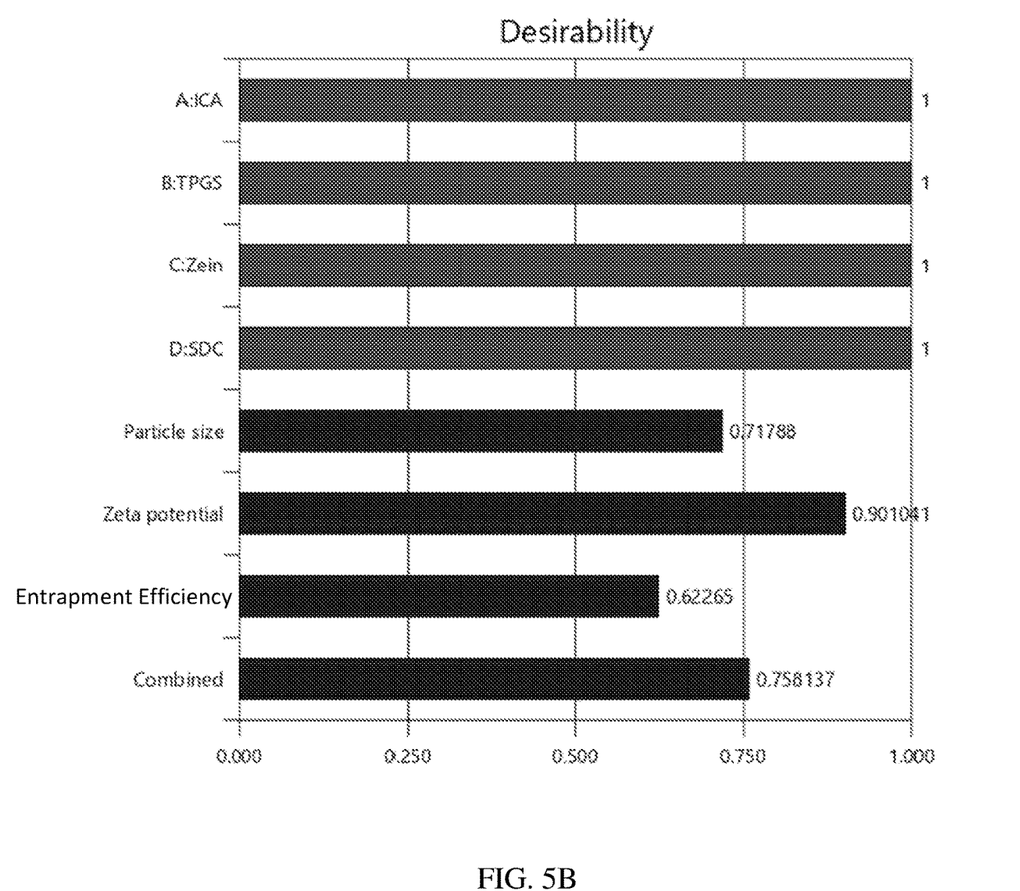

Numerical optimization and the desirability approach were implemented to predict the optimized variables' levels that, upon combination, could result in minimized size and maximized zeta potential and ICA entrapment. The ramp graphs presented in FIG. 5A shows the optimized levels and the predicted responses, while the desirability for each response and the overall desirability are graphically illustrated in FIG. 5B. The measured particle size of 224.45 nm, zeta potential of 0.961 mV, and drug entrapment of 65.29% coincide well with the predicted ones showing relative percentage error of 1.69%, 1.26% and 4.66%, respectively. The relatively small computed percentage errors prove the reliability of the optimization process.

In Vivo Investigation

Effect of Optimized ICA-Tocozeinolate Nanospheres on Male Rat Sexual Behavior

Figure 6:
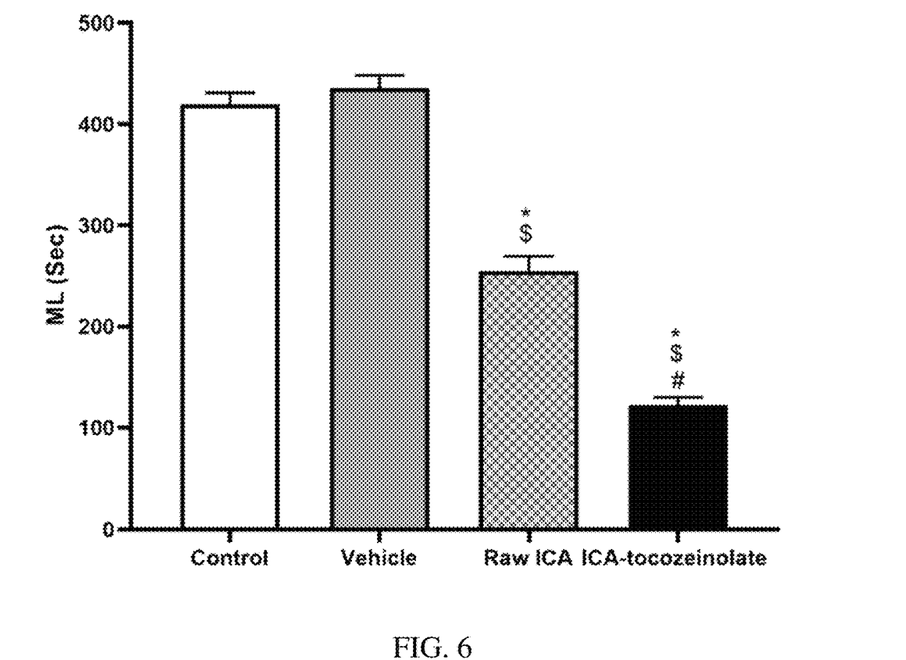
FIG. 6. Effect of optimized ICA-tocozeinolate on ML. ML=Mount Latency=Time (in seconds) from the introduction of the female to the first mount. *Significantly different vs control; <sup>&</sup> significantly different vs vehicle treated control; <sup>#</sup>Significantly different vs ICA.
Figure 7:
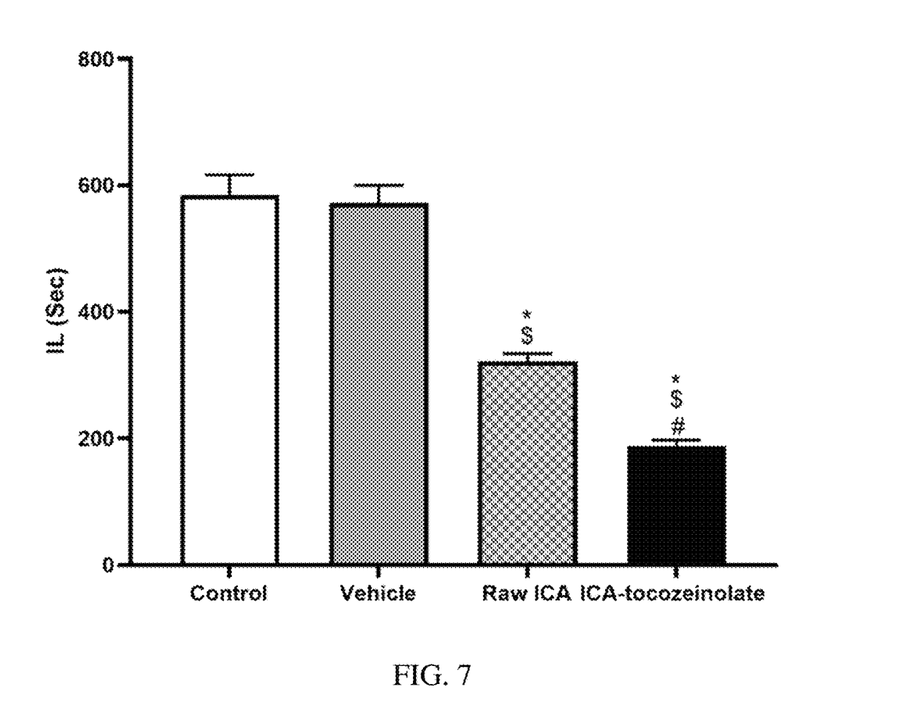
FIG. 7. Effect of optimized ICA-tocozeinolate on IL. IL=Intromission latency=Time (in seconds) from introduction of the female to the first intromission (vaginal penetration) *Significantly different vs control; <sup>&</sup> significantly different vs vehicle treated control; <sup>#</sup>Significantly different vs ICA.
Figure 8:
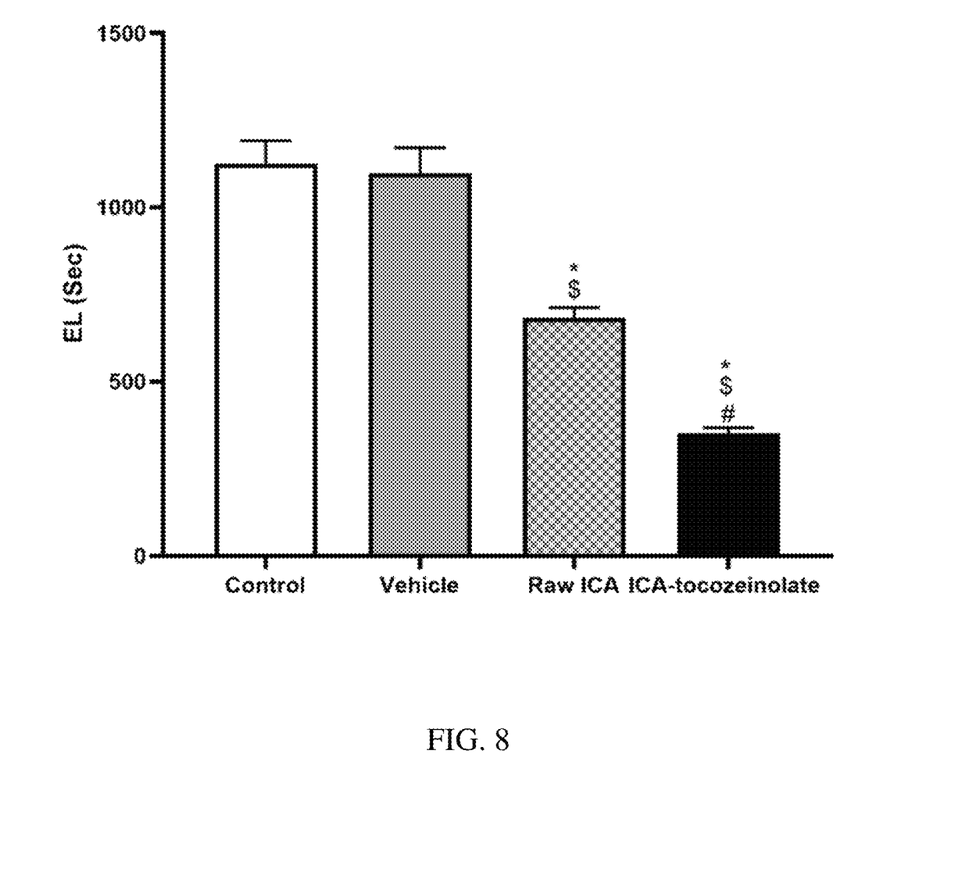
FIG. 8. Effect of optimized ICA-tocozeinolate on IL. EL=Ejaculation Latency=Time (in seconds) from the first intromission to ejaculation*Significantly different vs control; <sup>&</sup> significantly different vs vehicle treated control; <sup>#</sup>Significantly different vs ICA.

Oral administration of optimized ICA-tocozeinolate nanospheres resulted in an enhancement of male rat sexual behavior as compared to raw ICA at equivalent doses (20 mg/kg). This was evidenced by decreased average time of ML to almost half that of Raw ICA (FIG. 6). Also, IL time was reduced by 41% when compared to the raw ICA (FIG. 7). In addition, the optimized ICA-tocozeinolate reduced time of EL to almost half that of raw (FIG. 8). ICA has been used as a tonic drug in traditional Chinese medicine for centuries. It is believed to be a potent enhancer of erectile function. *Epimedium* extract is rich in ICA that shows vasodilating effects mediated by NO release. The extract performs a vaso-kinetic activity on the arteries and arterioles [8,34]. It was established that ICA is a cGMP-specific A phosphodiesterase type 5 inhibitor (PDE5) inhibitor that may be developed into an oral effective agent for the treatment of erectile dysfunction [12,21]. ICA has been found to evoke neuroprotective effects both in vivo and in vitro. ICA can significantly improve dopaminergic neuronal loss and neuroinflammation in mice [36]. Furthermore, ICA ameliorates lipopolysaccharide induced brain dysfunction, as well as corticosterone-induced apoptosis in neurons. [37-39].

Of great interest were the results showing that ICA not only inhibited MAO-A and MAO-B activities, but also elevated the decreased brain monoamine neurotransmitter levels induced experimentally. Therefore, ICA enhanced brain monoamines content, particularly dopamine [37]. Incidentally, decreased male sexual desire has been linked to decreased dopamine levels. This was confirmed by the observation that the use of dopamine receptor agonist apomorphine for the treatment of erectile dysfunction provides a strong support in favour of a participation of the dopaminergic system in the control of sexual function [40]. Thus, it can be suggested that ICA enhances male libido, at least partly, via boosting dopamine system in different brain areas. Based on these results, the optimized ICA-tocozeinolate nanospheres formula is useful for improving the delivery and efficacy of therapeutic agents.

REFERENCES

[1] Wang L, Li Y, Guo Y, Ma R, Fu M, Niu J, et al. *Herba Epimedii*: An Ancient Chinese Herbal Medicine in the Prevention and Treatment of Osteoporosis. Curr Pharm Des 2016; 22:328-49. https://doi.org/10.2174/1381612822666151112145907.

[2] Tan H M, Low W Y, Ng C J, Chen K K, Sugita M, Ishii N, et al. Prevalence and correlates of erectile dysfunction (E D) and treatment seeking for E D in asian men: The asian men's attitudes to life events and sexuality (MALES) study. J Sex Med 2007; 4:1582-92. https://doi.org/10.1111/j.1743-6109.2007.00602.x.

[3] Angeloni C, Barbalace M C, Hrelia S. Icariin and its metabolites as potential protective phytochemicals against Alzheimer's disease. Front Pharmacol 2019; 10:271. https://doi.org/10.3389/fphar.2019.00271.

[4] Fang J, Zhang Y. Icariin, an anti-atherosclerotic drug from chinese medicinal herb horny goat weed. Front Pharmacol 2017; 8:734. https://doi.org/10.3389/fphar.2017.00734.

[5] Jia G, Zhang Y, Li W, Dai H. Neuroprotective role of icariin in experimental spinal cord injury via its antioxidant, anti-neuroinflammatory and anti-apoptotic properties. Mol Med Rep 2019; 20:3433-9. https://doi.org/10.3892/mmr.2019.10537.

[6] Kong L, Liu J, Wang J, Luo Q, Zhang H, Liu B, et al. Icariin inhibits TNF-α/IFN-γ induced inflammatory response via inhibition of the substance P and p38-MAPK signaling pathway in human keratinocytes. Int Immunopharmacol 2015; 29:401-7. https://doi.org/10.1016/j.intimp.2015.10.023.

[7] Wu H, Kim M, Han J. Icariin metabolism by human intestinal microflora. Molecules 2016; 21. https://doi.org/10.3390/molecules21091158.

[8] Cao Y F, He R R, Cao J, Chen J X, Huang T, Liu Y. Drug-drug interactions potential of icariin and its intestinal metabolites via inhibition of intestinal UDP-glucuronosyltransferases. Evidence-Based Complement Altern Med 2012; 2012. https://doi.org/10.1155/2012/395912.

[9] Alhakamy N A, Fahmy U A, Badr-Eldin S M, Ahmed O A A, Asfour H Z, Aldawsari H M, et al. Optimized icariin phytosomes exhibit enhanced cytotoxicity and apoptosis-inducing activities in ovarian cancer cells. Pharmaceutics 2020; 12:346. https://doi.org/10.3390/pharmaceutics12040346.

[10] Parveen S, Sahoo S K. Polymeric nanoparticles for cancer therapy. J Drug Target 2008; 16:108-23. https://doi.org/10.1080/10611860701794353.

[11] Regier M C, Taylor J D, Borcyk T, Yang Y, Pannier A K. Fabrication and characterization of DNA-loaded zein nanospheres. J Nanobiotechnology 2012; 10:44. https://doi.org/10.1186/1477-3155-10-44.

[12] Weissmueller N T, Lu H D, Hurley A, Prud'Homme R K. Nanocarriers from GRAS Zein Proteins to Encapsulate Hydrophobic Actives. Biomacromolecules 2016; 17:3828-37. https://doi.org/10.1021/acs.biomac.6b01440.

[13] Ates M, Kaynak M S, Sahin S. Effect of permeability enhancers on paracellular permeability of acyclovir. J Pharm Pharmacol 2016; 68:781-90. https://doi.org/10.1111/jphp.12551.

[14] Conacher M, Alexander J, Brewer J M. Oral immunisation with peptide and protein antigens by formulation in lipid vesicles incorporating bile salts (bilosomes). Vaccine 2001; 19:2965-74. https://doi.org/10.1016/S0264-410X(00)00537-5.

[15] Khurana R K, Gaspar B L, Welsby G, Katare O P, Singh K K, Singh B. Improving the biopharmaceutical attributes of mangiferin using vitami E-TPGS co-loaded self-assembled phosholipidic nano-mixed micellar systems. Drug Deliv Transl Res 2018; 8:617-32. https://doi.org/10.1007/s13346-018-0498-4.

[16] Ahmed O A A, El-Say K M, Aljaeid B M B M, Badr-Eldin S M S M, Ahmed T A T A, Ahmed, O. A. A. E-SKM, et al. Optimized vinpocetine-loaded vitamin E D-α-tocopherol polyethylene glycol 1000 succinate-alpha lipoic acid micelles as a potential transdermal drug delivery system: In vitro and ex vivo studies. Int J Nanomedicine 2018; 14:33-43. https://doi.org/10.2147/IJN.S187470.

[17] Mi Y, Zhao J, Feng S-S. Vitamin E TPGS prodrug micelles for hydrophilic drug delivery with neuroprotective effects. Int J Pharm 2012; 438:98-106. https://doi.org/10.1016/j.ijpharm.2012.08.038.

Gorain B, Choudhury H, Pandey M, Kesharwani P. Paclitaxel loaded vitamin E-TPGS nanoparticles for cancer therapy. Mater Sci Eng C 2018; 91:868-80. https://doi.org/10.1016/j.msec.2018.05.054.

[19] Neophytou C M, Constantinou A I. Drug delivery innovations for enhancing the anticancer potential of vitamin e isoforms and their derivatives. Biomed Res Int 2015; 2015. https://doi.org/10.1155/2015/584862.

[20] Malmnäs C O, Meyerson B J. P-chlorophenylalanine and copulatory behaviour in the male rat [8]. Nature 1971; 232:398-400. https://doi.org/10.1038/232398a0.

[21] Ezzat S M, Ezzat M I, Okba M M, Hassan S M, Alkorashy A I, Karar M M, et al. Brain Cortical and Hippocampal Dopamine: A New Mechanistic Approach for *Eurycoma longifolia* Well-Known Aphrodisiac Activity and Its Chemical Characterization. Evidence-Based Complement Altern Med 2019; 2019. https://doi.org/10.1155/2019/7543460.

[22] Fahmy U A, Badr-Eldin S M, Ahmed O A A, Aldawsari H M, Tima S, Asfour H Z, et al. Intranasal niosomal in situ gel as a promising approach for enhancing flibanserin bioavailability and brain delivery: In vitro optimization and ex vivo/in vivo evaluation. Pharmaceutics 2020; 12:485. https://doi.org/10.3390/pharmaceutics12060485.

[23] Han D, Qi H, Huang K, Li X, Zhan Q, Zhao J, et al. The effects of surface charge on the intra-tumor penetration of drug delivery vehicles with tumor progression. J Mater Chem B 2018; 6:3331-9. https://doi.org/10.1039/c8tb00038g.

[24] Sharma S, Shukla P, Misra A, Mishra P R. Interfacial and colloidal properties of emulsified systems: Pharmaceutical and biological perspective. Pharmaceutical and biological perspective. Colloid Interface Sci. Pharm. Res. Dev., Elsevier Inc.; 2014, p. 149-72. https://doi.org/10.1016/B978-0-444-62614-1.00008-9.

[25] Yingchoncharoen P, Kalinowski D S, Richardson D R. Lipid-based drug delivery systems in cancer therapy: What is available and what is yet to come. Pharmacol Rev 2016; 68:701-87. https://doi.org/10.1124/pr.115.012070.

[26] Zhang Y R, Lin R, Li H J, He W ling, Du J Z, Wang J. Strategies to improve tumor penetration of nanomedicines through nanoparticle design. Wiley Interdiscip Rev Nanomedicine Nanobiotechnology 2019; 11:e1519. https://doi.org/10.1002/wnan.1519.

[27] Badr-Eldin S M, Aldawsari H M, Ahmed O A A, Alhakamy N A, Neamatallah T, Okbazghi S Z, et al. Optimized semisolid self-nanoemulsifying system based on glyceryl behenate: A potential nanoplatform for enhancing antitumor activity of raloxifene hydrochloride in MCF-7 human breast cancer cells. Int J Pharm 2021; 600:120493. https://doi.org/10.1016/j.ijpharm.2021.120493.

[28] Lazaridou M, Christodoulou E, Nerantzaki M, Kostoglou M, Lambropoulou D A, Katsarou A, et al. Formulation and in-vitro characterization of chitosan-nanoparticles loaded with the iron chelator deferoxamine mesylate (DFO). Pharmaceutics 2020; 12. https://doi.org/10.3390/pharmaceutics12030238.

[29] Gagliardi A, Bonacci S, Paolino D, Celia C, Procopio A, Fresta M, et al. Paclitaxel-loaded sodium deoxycholate-stabilized zein nanoparticles: characterization and in vitro cytotoxicity. Heliyon 2019; 5:e02422. https://doi.org/10.1016/j.heliyon.2019.e02422.

[30] Gagliardi A, Paolino D, Iannone M, Palma E, Fresta M, Cosco D. Sodium deoxycholate-decorated zein nanoparticles for a stable colloidal drug delivery system. hit J Nanomedicine 2018; 13:601-14. https://doi.org/10.2147/IJN.S156930.

[31] Krasnici S, Werner A, Eichhorn M E, Schmitt-Sody M, Pahernik S A, Sauer B, et al. Effect of the surface charge of liposomes on their uptake by angiogenic tumor vessels. hit J Cancer 2003; 105:561-7. https://doi.org/10.1002/ijc.11108.
[32] Wang H X, Zuo Z Q, Du J Z, Wang Y C, Sun R, Cao Z T, et al. Surface charge critically affects tumor penetration and therapeutic efficacy of cancer nanomedicines. Nano Today 2016; 11:133-44. https://doi.org/10.1016/j.nantod.2016.04.008.
[33] Saadat M, Zahednezhad F, Zakeri-Milani P, Heidari H R, Shahbazi-Mojarrad J, Valizadeh H. Drug targeting strategies based on charge dependent uptake of nanoparticles into cancer cells. J Pharm Pharm Sci 2019; 22:191-220. https://doi.org/10.18433/jpps30318.
[34] Deo N, Jockusch S, Turro N J, Somasundaran P. Surfactant interactions with zein protein. Langmuir 2003; 19:5083-8. https://doi.org/10.1021/la020854s.
[35] Gagliardi A, Voci S, Salvatici M C, Fresta M, Cosco D. Brij-stabilized zein nanoparticles as potential drug carriers. Colloids Surfaces B Biointerfaces 2021; 201:111647. https://doi.org/10.1016/j.colsurfb.2021.111647.
[36] Hijikata Y, Yasuhara A, Medicine Y Y- . . . C, 2006 undefined. Traditional Chinese medicine treatment of epilepsy. LiebertpubCom n.d.
[37] Wu Y, Wang L, Hu K, Yu C, Zhu Y, . . . S Z-F in, et al. Mechanisms and therapeutic targets of depression after intracerebral hemorrhage. FrontiersinOrg n.d.
[38] Zheng J, Hu S, Wang J, Zhang X, . . . D Y-P, 2021 undefined. Icariin improves brain function decline in aging rats by enhancing neuronal autophagy through the AMPK/mTOR/ULK1 pathway. Taylor Fr n.d.
[39] Wu Y, Wang L, Hu K, Yu C, Zhu Y, Zhang S, et al. Mechanisms and therapeutic targets of depression after intracerebral hemorrhage. Front Psychiatry 2018; 9. https://doi.org/10.3389/FPSYT.2018.00682/FULL.
[40] Giuliano F, Allard J. Dopamine and sexual function. Int J Impot Res 2001; 13 Suppl 3:S18-28. https://doi.org/10.1038/SJ.IJIR.3900719.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A composition comprising:
    0.4-0.8 wt % of zein nanoparticles, wherein the zein nanoparticles are formed only from zein;
    icariin (ICA) or a pharmaceutically acceptable salt thereof encapsulated within the zein nanoparticles;
    4-6 wt % of at least one solubilizer, wherein the at least one solubilizer comprises D-a-Tocopherol polyethylene glycol 1000 succinate (TPGS); and
    0.2-0.4 wt % of one or more pharmaceutical penetration enhancers.

2. The composition of claim 1, wherein ICA or the pharmaceutically acceptable salt thereof is present in an amount of 0.4-0.8 wt %.

3. The composition of claim 1, wherein the zein nanoparticles have an average diameter of 220-230 nm.

4. The composition of claim 1, wherein the one or more pharmaceutical penetration enhancers are selected from the group consisting of, bile salts, terpenes, sulphoxides, azones, alcohols, and alkanols.

5. The composition of claim 1, wherein the one or more pharmaceutical penetration enhancers comprises sodium deoxycholate.

6. The composition of claim 1, wherein the composition has a zeta potential of 0.8-1.1 mV.

7. A method of enhancing libido in a subject in need thereof, comprising administering an effective amount of the composition of claim 1 to the subject.

8. The method of claim 7, wherein the composition is orally administered.

9. The method of claim 7, wherein the subject is male.

10. The composition of claim 1, wherein ICA or the pharmaceutically acceptable salt thereof is the sole active agent in the composition.

11. The composition of claim 1, wherein the composition is configured for oral administration.

* * * * *